(12) United States Patent
Cole et al.

(10) Patent No.: US 7,586,114 B2
(45) Date of Patent: Sep. 8, 2009

(54) OPTICAL CAVITY SYSTEM HAVING AN ORTHOGONAL INPUT

(75) Inventors: Barrett E. Cole, Bloomington, MN (US); James A. Cox, New Brighton, MN (US); J. David Zook, Golden Valley, MN (US)

(73) Assignee: Honeywell International Inc., Morristown, NJ (US)

( * ) Notice: Subject to any disclaimer, the term of this patent is extended or adjusted under 35 U.S.C. 154(b) by 147 days.

(21) Appl. No.: 11/770,648

(22) Filed: Jun. 28, 2007

(65) Prior Publication Data

US 2009/0014670 A1   Jan. 15, 2009

Related U.S. Application Data

(63) Continuation-in-part of application No. 11/633,872, filed on Dec. 4, 2006, which is a continuation-in-part of application No. 10/953,174, filed on Sep. 28, 2004, now Pat. No. 7,145,165.

(51) Int. Cl.
*G01N 21/49* (2006.01)
*G01N 21/51* (2006.01)

(52) U.S. Cl. ........................ 250/575; 250/576; 356/437; 356/440

(58) Field of Classification Search ................. 250/575, 250/576; 356/437, 440
See application file for complete search history.

(56) References Cited

U.S. PATENT DOCUMENTS

| | | | |
|---|---|---|---|
| 4,233,568 A | 11/1980 | Hamerdinger et al. | |
| 4,612,647 A | 9/1986 | Norvell | |
| 4,614,961 A | 9/1986 | Khan et al. | |
| 4,672,624 A * | 6/1987 | Ford ........................... | 372/87 |
| 4,870,224 A | 9/1989 | Smith et al. | |
| 4,973,131 A | 11/1990 | Carnes | |

(Continued)

FOREIGN PATENT DOCUMENTS

DE   3311808   10/1984

(Continued)

OTHER PUBLICATIONS

Bernstein et al., "Development of a Miniature Silicon PhotoAcoustic Gas Sensor", Presented at Opto 96, Leipzig, Germany, 6 pages, Sep. 26-29, 1999.

(Continued)

*Primary Examiner*—Stephen Yam
(74) *Attorney, Agent, or Firm*—Kris T. Fredrick

(57) ABSTRACT

An optical system having a closed loop light path with a source for providing light in a direction parallel to the normal of an input to the light path. The light may be provided via a refracting mechanism to the input. The system may be a cavity ring-down sensor or some other optical device. The light path may be formed in a laser gyroscope type cavity. A light source may have a beam aligned to a spot, indicator or indicator or mark may be determined in accordance with parameters of the refracting mechanism and/or cavity. A fixture for holding the light source may be secured so that placement of the source in the fixture will automatically result in an aligned light source. Then the refracting mechanism may be inserted to further complete fabrication of the optical system.

20 Claims, 14 Drawing Sheets

U.S. PATENT DOCUMENTS

| | | | |
|---|---|---|---|
| 5,022,745 A | 6/1991 | Zayhowski et al. | |
| 5,040,895 A | 8/1991 | Laurent et al. | |
| 5,135,304 A | 8/1992 | Miles et al. | |
| 5,146,465 A | 9/1992 | Khan et al. | |
| 5,278,435 A | 1/1994 | Van Hove et al. | |
| 5,408,319 A | 4/1995 | Halbout et al. | |
| 5,418,868 A | 5/1995 | Cohen et al. | |
| 5,450,053 A | 9/1995 | Wood | |
| 5,468,910 A | 11/1995 | Knapp et al. | |
| 5,512,750 A | 4/1996 | Yanka et al. | |
| 5,528,040 A | 6/1996 | Lemann | |
| 5,550,373 A | 8/1996 | Cole et al. | |
| 5,629,951 A | 5/1997 | Chang-Hasnain et al. | |
| 5,677,538 A | 10/1997 | Moustakas et al. | |
| 5,679,965 A | 10/1997 | Schetzina | |
| 5,723,706 A | 3/1998 | Brasier et al. | |
| 5,739,554 A | 4/1998 | Edmond et al. | |
| 5,834,331 A | 11/1998 | Razeghi | |
| 5,835,231 A * | 11/1998 | Pipino | 356/440 |
| 5,847,397 A | 12/1998 | Moustakas | |
| 5,869,896 A | 2/1999 | Baker et al. | |
| 5,900,650 A | 5/1999 | Nitta | |
| 5,909,280 A | 6/1999 | Zavracky | |
| 5,912,740 A | 6/1999 | Zare et al. | |
| 5,915,051 A | 6/1999 | Damask et al. | |
| 5,933,565 A | 8/1999 | Diebold | |
| 5,960,025 A | 9/1999 | Thorland et al. | |
| 6,040,895 A | 3/2000 | Haas | |
| 6,080,988 A | 6/2000 | Ishizuya et al. | |
| 6,084,682 A | 7/2000 | Zare et al. | |
| 6,091,504 A | 7/2000 | Walker et al. | |
| 6,115,122 A | 9/2000 | Bao et al. | |
| 6,122,416 A | 9/2000 | Ooba et al. | |
| 6,147,756 A | 11/2000 | Zavracky et al. | |
| 6,208,798 B1 | 3/2001 | Morozov et al. | |
| 6,233,052 B1 * | 5/2001 | Zare et al. | 356/437 |
| 6,287,940 B1 | 9/2001 | Cole et al. | |
| 6,295,130 B1 | 9/2001 | Sun et al. | |
| 6,296,779 B1 | 10/2001 | Clark et al. | |
| 6,310,904 B1 | 10/2001 | Thorland et al. | |
| 6,324,192 B1 | 11/2001 | Tayebati | |
| 6,335,669 B1 | 1/2002 | Miyazaki et al. | |
| 6,380,531 B1 | 4/2002 | Sugihwo et al. | |
| 6,384,953 B1 | 5/2002 | Russell et al. | |
| 6,404,648 B1 | 6/2002 | Slupe et al. | |
| 6,406,578 B1 | 6/2002 | Schober et al. | |
| 6,421,127 B1 | 7/2002 | McAndrew et al. | |
| 6,424,419 B1 * | 7/2002 | Tazartes et al. | 356/473 |
| 6,438,149 B1 | 8/2002 | Tayebati et al. | |
| 6,452,680 B1 | 9/2002 | Paldus et al. | |
| 6,483,130 B1 | 11/2002 | Yang et al. | |
| 6,492,726 B1 | 12/2002 | Quek et al. | |
| 6,507,107 B2 | 1/2003 | Vaiyapuri | |
| 6,545,739 B1 | 4/2003 | Matsumoto et al. | |
| 6,583,917 B2 | 6/2003 | Melloni et al. | |
| 6,584,126 B2 | 6/2003 | Wang et al. | |
| 6,590,710 B2 | 7/2003 | Hara et al. | |
| 6,594,059 B2 | 7/2003 | Flanders | |
| 6,597,713 B2 | 7/2003 | Ouchi | |
| 6,608,711 B2 | 8/2003 | Flanders et al. | |
| 6,627,983 B2 | 9/2003 | Tu et al. | |
| 6,658,034 B2 | 12/2003 | Garnache et al. | |
| 6,670,599 B2 | 12/2003 | Wagner et al. | |
| 6,728,286 B2 | 4/2004 | Thorland et al. | |
| 6,784,946 B1 | 8/2004 | Schroter et al. | |
| 6,836,501 B2 | 12/2004 | Cox et al. | |
| 6,879,014 B2 | 4/2005 | Wagner et al. | |
| 6,985,281 B2 | 1/2006 | Wagner et al. | |
| 7,002,697 B2 | 2/2006 | Domash et al. | |
| 7,012,696 B2 | 3/2006 | Orr et al. | |
| 7,015,457 B2 | 3/2006 | Cole et al. | |
| 7,046,362 B2 | 5/2006 | Lehmann et al. | |
| 7,049,004 B2 | 5/2006 | Domash et al. | |
| 7,089,781 B2 | 8/2006 | Petrovic et al. | |
| 7,106,763 B2 | 9/2006 | Tan et al. | |
| 7,113,256 B2 | 9/2006 | Butler et al. | |
| 7,145,165 B2 | 12/2006 | Cox et al. | |
| 7,147,165 B2 | 12/2006 | Mongin et al. | |
| 7,147,695 B2 | 12/2006 | Mitra | |
| 7,221,827 B2 | 5/2007 | Domash et al. | |
| 7,304,799 B2 | 12/2007 | Ma et al. | |
| 2002/0191268 A1 | 12/2002 | Seeser et al. | |
| 2003/0107739 A1 * | 6/2003 | Lehmann et al. | 356/437 |
| 2004/0234198 A1 | 11/2004 | Wagner et al. | |
| 2004/0255853 A1 | 12/2004 | Ma et al. | |
| 2005/0030628 A1 | 2/2005 | Wagner et al. | |
| 2005/0082480 A1 | 4/2005 | Wagner et al. | |
| 2005/0105184 A1 | 5/2005 | Ma et al. | |
| 2005/0254056 A1 | 11/2005 | Kachanov et al. | |
| 2007/0133001 A1 | 6/2007 | Cox et al. | |

FOREIGN PATENT DOCUMENTS

| | | |
|---|---|---|
| DE | 19635421 | 12/1997 |
| EP | 0177918 | 3/1991 |
| EP | 0667548 | 1/1995 |
| EP | 1069658 | 1/2001 |
| EP | 1061618 | 11/2007 |
| JP | 03252172 | 11/1991 |
| JP | 05095130 | 4/1993 |
| JP | 7288334 | 10/1995 |
| WO | 9326049 | 12/1993 |
| WO | 9942875 | 8/1999 |

OTHER PUBLICATIONS

Brown, et al., "Visible-Blind UV Digital Camera Based on a 32*32 Array of GAN/AIGAN P-I-N Photodiodes", MRS Internet Journal of Nitride Semiconductor Research, vol. 4S1, pp. 1-10, Sep. 1999.

Campargue et al., "Measurement of SiH2 Density in a Discharge by Intracavity Laser Absorption Spectroscopy and CW Cavity Ring-Down Spectroscopy," Journal of Physics D. Applied Physics, vol. 31, No. 10 pp. 1168-1175, May 21, 1998.

Chitica et al., "Monolithic InP-Based Tunable Filter with 10-nm Bandwidth for Optical Data Interconnects in the 1550-nm Band," IEEE Photonics Technology Letters, vol. 11, No. 5, pp. 584-586, May 1999.

Chou et al., "Diode-Laser Measurements of He-, Ar-, and N2-Broadened HF Lineshapes in the First Overtone Band," Journal of Molecular Spectroscopy 196, pp. 70-76, 1999.

Chung et al., "Design and Fabrication of 10×10 Micro-Spatial Light Modulator Array for Phase and Amplitude Modulation," Sensors and Actuators, vol. 78, No. 1, pp. 63-70, Jan. 1999.

Cole et al., "Microscopic Spectroscopy of Optical MEMS Devices," Topic 2 (Materials and Technology), Honeywell Laboratories, 2 pages, on or Around Dec. 11, 2000.

Edwards, "Multiple-Traverse Absorption Cell Design," Journal of the Optical Society of America, vol. 51, No. 1, pp. 98-102.

Ferber et al., "A Miniature Silicon Photoacoustic Detector for Gas Monitoring Applications", presented at the MTEX International Conference on Sensors and Transducers, Birmingham, UK, 7 pages, Feb. 14, 2001.

Jerman et al., "A Miniature Fabry-Perot Interferometer with a Corrugated Silicon Diaphragm Support," Sensors and Actuators, vol. A29, No. 2, pp. 151-158, Nov. 1991.

Kurochkin et al., "Complex-Cavity Two-Mode CO2 Laser for Saturated Intracavity Absorption Spectroscopy," Optical Spectroscopy, vol. 68, No. 6, pp. 793-797, 1990.

Kurochkin et al., "Three-Mirror Cavity CO2 Laser for Intracavity Saturated-Absorption Spectroscopy," Optical Spectroscopy, vol. 65, No. 2, pp. 265-267, 1988.

O'Keefe et al., "Cavity Ring-Down Optical Spectrometer for Absorption Measurements Using Pulsed Laser Sources," Review of Scientific Instruments, 59, 11 pages, 1988.

Paul et al., "Cavity Ringdown Measures Trace Concentrations," Laser Focus World, pp. 71-80, Mar. 1997.

Richman et al., "Continuously Tunable, Single-Longitudinal-Mode, Pulsed Mid-Infrared Optical Parametric Oscillator Based on Periodically Poled Lithium Niobate," Optical Society of America, vol. 17, No. 7, pp. 1233-1239.

Sadeghi et al., "Cavity Ring Down Spectroscopy Applied to Plasma Diagnostics," Proc. Int. Symp. Laser-aided Plasma Diagnostics Lake Tahoe, CA, , 8 pages, Sep. 1999.

Scherer et al., "Infrared Cavity Ringdown Laser Absorption Spectroscopy (IR-CRLAS) in Low Pressure Flames," Applied Physics B., vol. 64, pp. 699-705, 1997.

Schweber, "An Old Communications Problem Reoccurs in Optical-Communication-System Design—How it Works: Making the Laser Diode Tunable", EDN, 3 pages, Sep. 28, 2000.

Shimizu et al., "Stark Spectroscopy by 10μ Lasers Using a Multipath Cell," Journal of Applied Physics, vol. 46, No. 1, pp. 258-259, Jan. 1975.

Smirnov et al., "Dye Lasers Using a Three-Mirror Cavity with Lamp Excitation," 4 pages, 1981.

Spence et al., "A Laser-Locked Cavity Ring-Down Spectrometer Employing an Analog Detection Scheme," Review of Scientific Instruments, vol. 71, No. 2, pp. 347-353, Feb. 2000.

Sze, "Physics of Semiconductor Devices." pp. 763-765, John Wiley & Sons, N.Y., 1982.

Tayebati et al., "Microelectromechanical Tunable Filter with Stable Half Symmetric Cavity," Electronics Letters, IEE Stevanage, GB, vol. 34, No. 20, pp. 1967-1968, Oct. 1998.

Tayebati et. al., "Widely Tunable Fabry-Perot Filters Using High Index-Contrast DBRs," Design and Manufacturing of WDM Devices, Dallas, Texas, Nov. 4-5, 1997, SPIE vol. 3234, pp. 206-218, 1998.

Yang et al., "Back-Illuminated GAN/AIGAN Heterojunction Photodiodes With High Quantum Efficiency and Low Noise," Applied Physics Letters, vol. 73, No. 8, pp. 1086-1088, XP000777678, Aug. 24, 1998.

Pipino et al., "Evanescent Wave Cavity Ring-Down Spectroscopy With a Total-Internal-Reflection Minicavity," Rev. Sci Instrum., vol. 8, No. 68, pp. 2978-2989, Aug. 1997.

Schiwon et al., "Terahertz Cavity-Enhanced Attenuated Total Reflection Spectroscopy," Applied Physics Letters, vol. 86, 3 pages, 2005.

* cited by examiner

OPTICAL CAVITY SYSTEM HAVING AN ORTHOGONAL INPUT

This application is a continuation-in-part of U.S. patent application Ser. No. 11/633,872, filed Dec. 4, 2006, which is a continuation-in-part of U.S. patent application Ser. No. 10/953,174, filed Sep. 28, 2004, now U.S. Pat. No. 7,145,165.

BACKGROUND

The invention pertains to optical systems having loop-like light paths, and particularly to paths having sample fluids inserted into them. More particularly, the invention pertains to light inputs to light paths of the systems.

SUMMARY

The invention is an optical system having a loop-like light path. The may be a light refracting mechanism situated between an input to the light path and a source of light for the optical system.

DESCRIPTION

Figure 1:
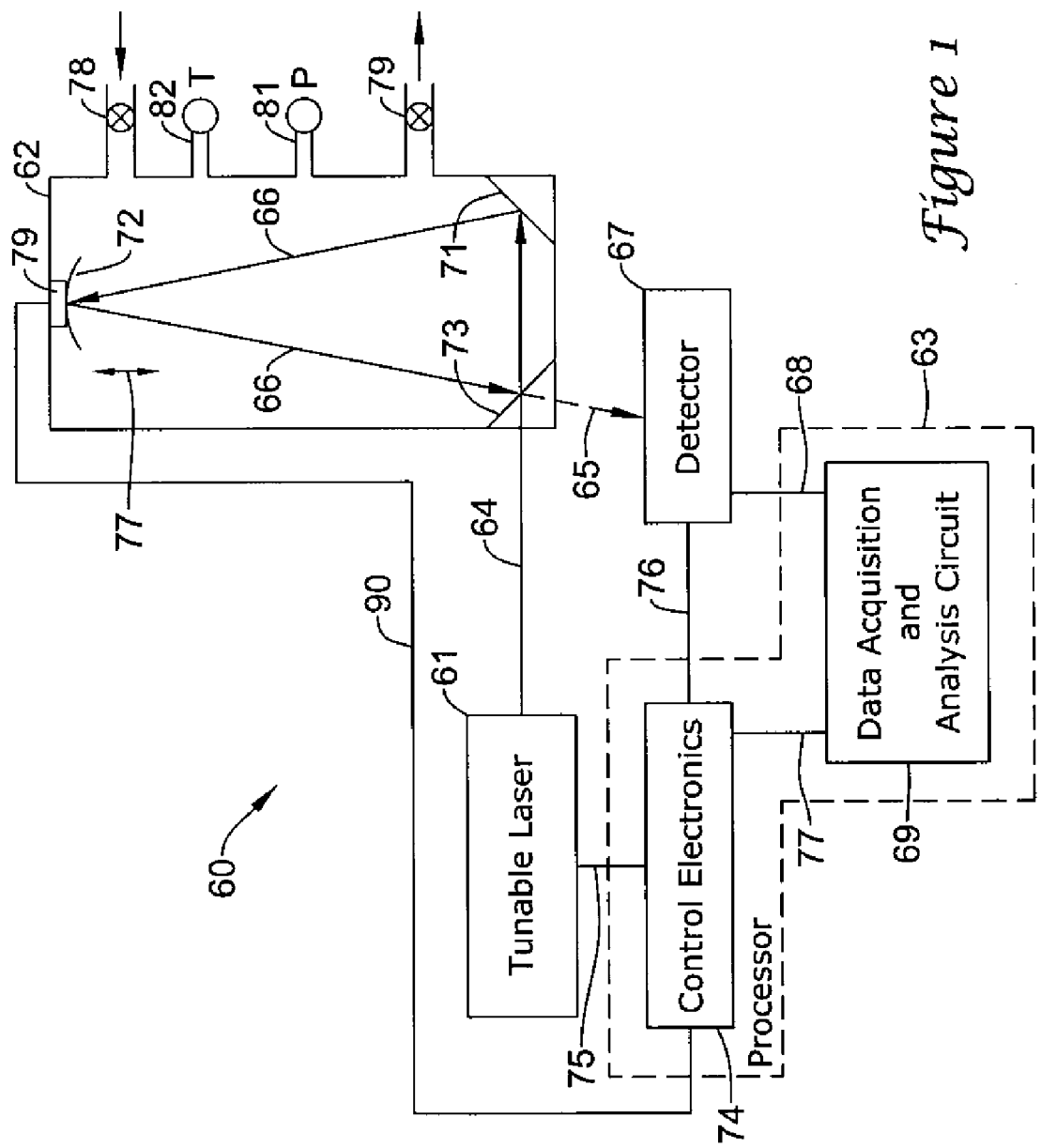
FIG. 1 is a diagram of a ring-down cavity.

As shown in FIG. 1, a tunable laser 61 may be coupled to a three mirror optical ring-down cavity 62. One of the mirrors, e.g., mirror 72, may have a slight and high radius curvature to improve stability so that a light beam 66 does not walk off the cavity. Cavity 62 may be a block ring cavity or, alternatively, a ring cavity akin to a cavity of laser system though not necessarily having two lasers going through it. Cavity 62 may have two, three, four mirrors, or any other number of mirrors providing a light path selected from various possible routes for light in the cavity. There may be an analog detection circuit 63 to extract the ring-down rate from an exponentially decaying ring-down waveform. A technique may be used to measure trace concentrations of gases in the near infrared region using a continuous wave excitation 64 of a cavity-ring down spectroscopy cell or cavity 62 (CW-CRDS). Cavity ring-down spectroscopy may be an absorption technique in which light 64 is coupled into a high finesse optical resonator 62. The cavity 62 may be tuned to the absorption line of the gas in the cavity being sensed and quantitatively measured. Cavity 62 may be tuned such that light 66 is in phase with the incoming light 64. This tuning, such as adjusting the path length of light 66, may be applicable to other kinds of cavities, such as those with two mirrors, four mirrors, and the like. Tuning the cavity with mirror 72 adjustment 77 with an actuator 79 may be one way of adjustment. Similarly, a light source 61 may have an output wavelength tuned to the absorption line of the gas in the cavity. By monitoring the decay rate of the light 66 inside the cavity with detection circuit 63 which includes a detector 67, one may determine a concentration of a particular gas in the cavity 62. The near infrared light 65 detected may contain vibrational overtone transitions and forbidden electronic transitions of various atmospheric species of gas. System 60 may obey Beer's law and provide a highly accurate concentration determination. The effective path length of the light 66 in the cavity may be about a hundred times larger than the physical size of the cell 62 due to highly reflective dielectric mirrors 71, 72 and 73. Mirror 72 may have an adjustment 77 for tuning the path length of cell 62 for light 66.

There may be fast trace gas impurity measurements of critical molecules such as $H_2O$, CO, $NH_3$, HF, HCl, $CH_4$ and $C_2H_2$. Such measurements may be made in seconds. Trace moisture concentration may be measured at levels from parts per billion (ppb) to parts per trillion (ppt).

Tunnel laser 61 may send a continuous wave (or possibly pulsed) light signal to cell 62. Signal 64 may be regarded as a signal 66 that is reflected around in cell 62 from mirror 71, to mirror 72, to mirror 73, to mirror 71 and so on until the signal 66 diminishes. Some light 65 may leave cell 62 and impinge detector 67. Detector 67 may convert light signal 65 to an electrical signal 68 that goes to a data acquisition and analysis unit 69. Control electronics 74 may send control signals 75, 76 and 77 to tunable laser 61, detector 65 and data acquisition and analysis unit 69, respectively. Also, a control signal 90 may be sent to a moveable support 79 of mirror 72 to provide tenability of the path for light 66. Support 79 may be a piezoelectric transducer to allow tuning and modulation of the path length of cell 62.

One may detect a certain fluid using a laser tuned on a transition band, near a particular frequency. Using system 62, one may be able to measure the concentration of the fluid in some medium. The certain fluid and associated medium may enter a port 78 and exit a port 79. Port 81 may be for a connection to a pump. Port 82 may be used for a gauge. One or more hollow optical fibers to and from the ring cavity may be used provide gas to take gas from the ring cavity. The gas may be compartmentalized in the cavity with Brewster windows.

The system 60 may provide for an intrinsic measure of absorption. The CRDS sensitivity may equal $$(\Delta t/t)(L_{opt}/L_{cav})(1/F_{acq})^{1/2}$$

Another relationship may be:

$$L_{opt} \sim L_{cav}/[n_{mirror}(1-R)] \sim 10^4 L_{cav}$$

Typical sensitivity may be at about $10^{-6}$ to $10^{-10}$ cm$^{-1}$ for multimode light and about $10^{-9}$ to $10^{-12}$ cm$^{-1}$ for single mode light.

The system 62 may be built on the strengths of a MEMS etalon, various laser system technologies and VCSELs.

Figure 2:
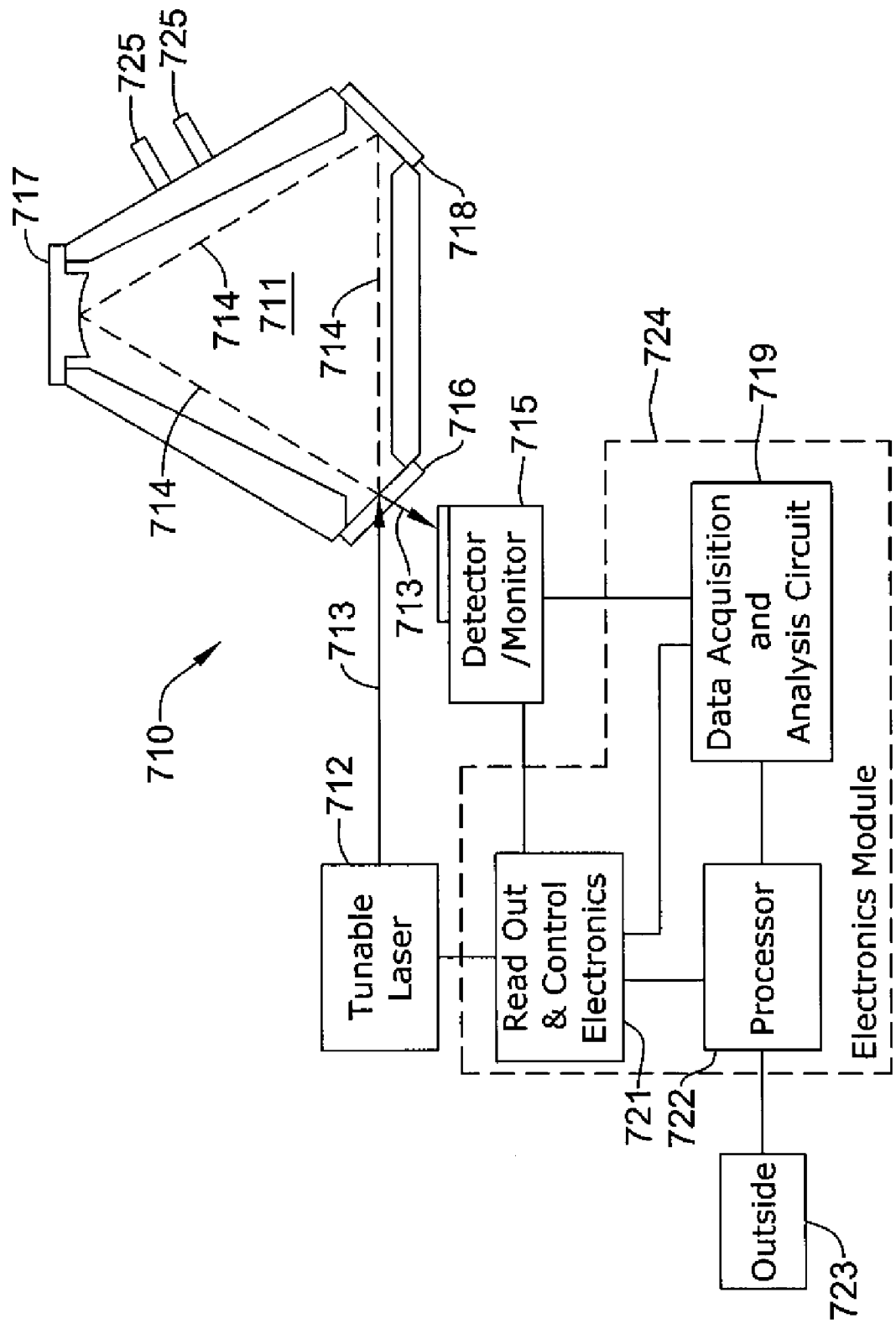
FIG. 2 is a diagram of a sensor system having a ring cavity which may be fabricated, formed, machined, or the like from one or several pieces of solid material.

FIG. 2 shows a sensor system 710 having a ring cavity 711. The cavity may be fabricated, formed or machined, or the like from one or several pieces of solid material. A light source 712 may emit a beam of light 713 into cavity 711. The beam of light may follow a path 714 of the cavity 711. Here, the light may propagate in a counterclockwise direction from the perspective of looking into the plane of the sheet of the Figure. A detector 715 may be proximate to where light 713 entered the cavity 711 from source 712. Source 712 may, for example, be a tunable laser.

At the corners of cavity 711, there may be mirrors 716, 717 and 718. Mirror 716 may partially reflect light 713 in the cavity so that detector 715 may detect some light in the cavity for analysis purposes. On mirror 716 may have a small hole for input and output for light 713. In this case, the mirror 716 may be fully reflective. Detection of light 713 may note intensity versus time, frequency, and other parameters as desired. The output of the detector or monitor 715 may go to a data acquisition and analysis circuit 719 for such things as acquisition, analysis and other purposes for obtaining information about a sample fluid in the cavity 711. One purpose may be for tuning the laser 712 to an adsorption line of the sample. The detector output to the readout and control electronics 721 may be improved with a dual JFET amplifier. Other circuits may be utilized for detector output processing. Readout and control electronics 721 may provide an excitation and control for light source 712. Inputs and outputs may be provided to and from a processor 722 relative to connections between the processor 722 and readout and control electronics 721 and data acquisition and analysis circuit 719. Processor 722 may also be connected to the outside 723 signals going in and out of system 710. A user interface may be effected with the readout and control electronics 721 and/or the outside 723. Readout and control electronics 721, data acquisition and analysis circuit 719, and processor 722 may constitute an electronics module 724. Electronics module 724 may have other components. Ports 725 may provide for input and output of a sample fluid to and from the cavity 711.

Figure 3:
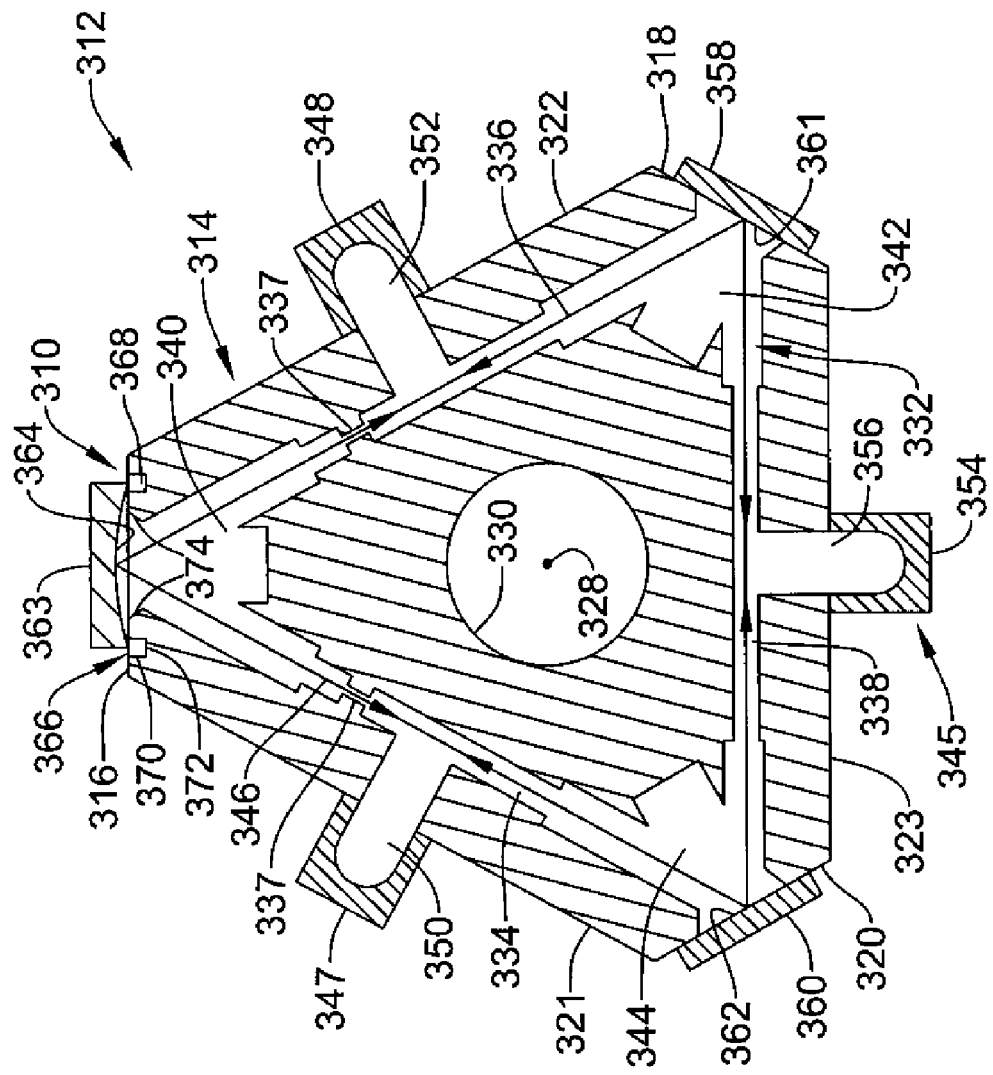
FIG. 3 is a diagram of the sensor system incorporating a machined-like block for the ring cavity.

A mirror mounting device 310 and approach for beam path alignment of a system 312 is illustrated generally in FIG. 3. The system 312 includes a system frame or block 314. The block 314 is generally triangular shaped with a hexagonal outer periphery. The shapes could be square, pentagon-like or other, along with various shapes for the periphery. The hexagonal outer periphery includes three planar non adjacent sides that form first, second and third mirror mounting surfaces 316, 318 and 320, respectively, and three further planar non adjacent sides 321, 322 and 323, respectively. The mounting surfaces 316, 318 and 320 and sides 321, 322 and 323 form a border for planar top and bottom surfaces 324 and 326, respectively, of the block 314. The block 314 is centered about an input axis 328 (which is perpendicular to top and bottom surfaces 324 and 326) within a circular inner boundary 330 of the block 314. The block 314 is formed of a glass ceramic or like material. Suitable block materials include the glass ceramic material marketed under the trademarks "Cervit" and "Zerodur". A suitable glass material is marketed under the trademark "BK-7".

As seen in FIG. 3, an internal optical cavity 332 of the block 314 comprises three substantially straight bores 334, 336 and 338, respectively that are interconnected at the mounting surfaces 316, 318 and 320 by three cylindrical shaped wells 340, 342 and 344, respectively. The block 314 may be solid and then machined to accommodate various shapes, channels, holes, bores, and spaces for operational aspects or for placement of components. The bores 334 and 336 include apertures 335 and 337, respectively that define a desired closed loop optical path. The bores 334, 336 and 338 and the wells 340, 342 and 344 are bored within the block 314 to form the triangular shaped closed loop optical path, with the mounting surfaces 316, 318 and 320 located at corners of the optical path.

As seen in FIG. 3, two planar mirrors 358 and 360, respectively, having flat reflective surfaces 361 and 362, respectively, are secured (for example, via optical contact, epoxy bonding or fritting) to the second and third mirror mounting surfaces 318 and 320, respectively. A curved mirror 363, having a concave reflective surface 364 is secured (via epoxy bonding or fritting) to the mirror mounting device 310 associated with the first mirror mounting surface 316. The reflective surfaces 361, 362 and 364 of each of the mirrors 358, 360 and 363 reflects the light beam(s) 346 at its respective corner of the closed loop optical path defined by the optical cavity 332. Mirror 358 and/or mirror 360 may have a partially reflective surface so that its respective port may be used as an input and/or an output for such applications as a cavity ring-down sensor as an illustrative example.

Trace gas detection and identification with very high sensitivity may be achieved using cavity-ring-down technique implemented with ring-laser gyro fabrication and alignment technology in order to achieve cost-effective producibility.

The advantages of adapting ring laser gyro fabrication methods (laser block, mirror fab, attachment, and alignment, and so forth) may achieve a cost-effective system for cavity-ring-down gas detection. The present system has an approach for coupling light into and out of the ring cavity. In particular, the approach provides for directing light incident from the source normally onto the optical input port of the ring cavity in order to facilitate alignment of the source to cavity, and then interposing a prism coupling module to direct the light into the ring cavity. A variation of this approach includes a modification of the coupling prism introduced before the optical input port so as to also couple light in the cavity to an external detector, thus allowing the same cavity port to be both an input and output port without return light being fed back into the source.

Figure 4:
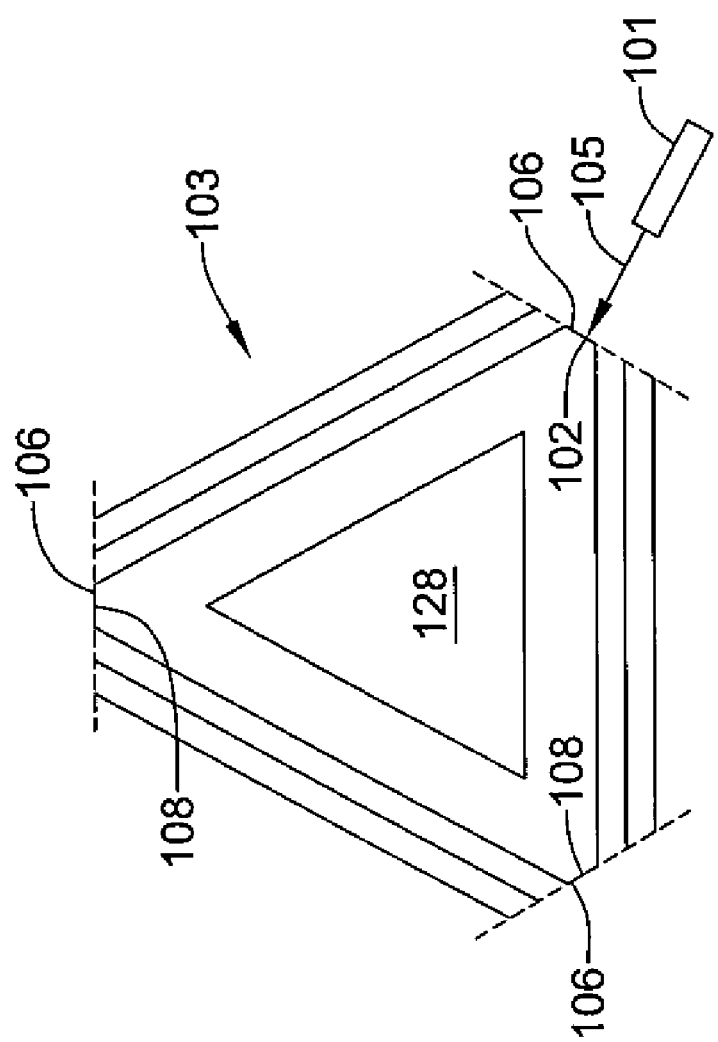
FIG. 4 is a diagram of a basic layout of a sensor upon which an illustrative example of the invention may be based.
Figure 5:
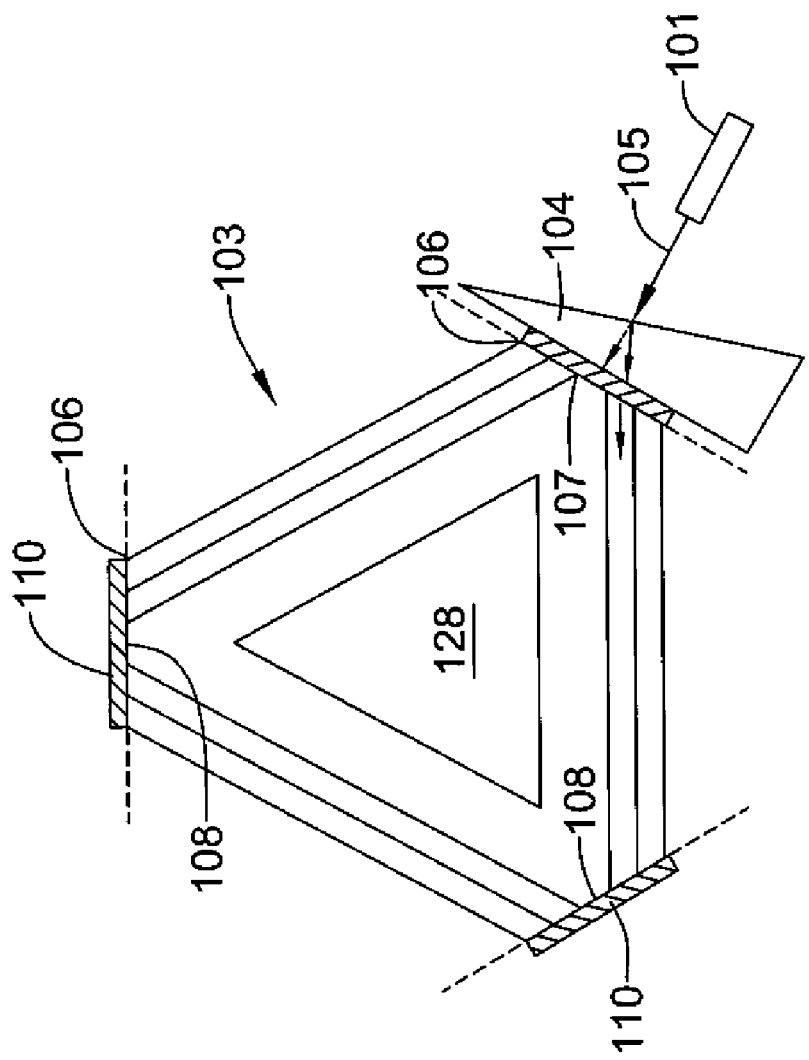
FIG. 5 is the diagram of the sensor of Figure with a refracting mechanism for light guidance.

FIG. 4 shows a basic layout of a ring cavity 103 with three corners 102 and 108 for reflecting light around in the cavity. Each of these corners has external polished surfaces 106. Inside portion 128 of cavity 103 need not be present. A light source 101 is shown aligned with the corner 102 as an input having a light 105 propagating in a direction approximately parallel to a normal of the input 102. FIG. 5 is a diagram of an approach for alignment of the light source 101 (such as a tunable laser) with the optical input port 102 of the ring-cavity 103 and an insertion of a prism coupling module 104 to direct the normally incident light into the cavity.

Figure 7:
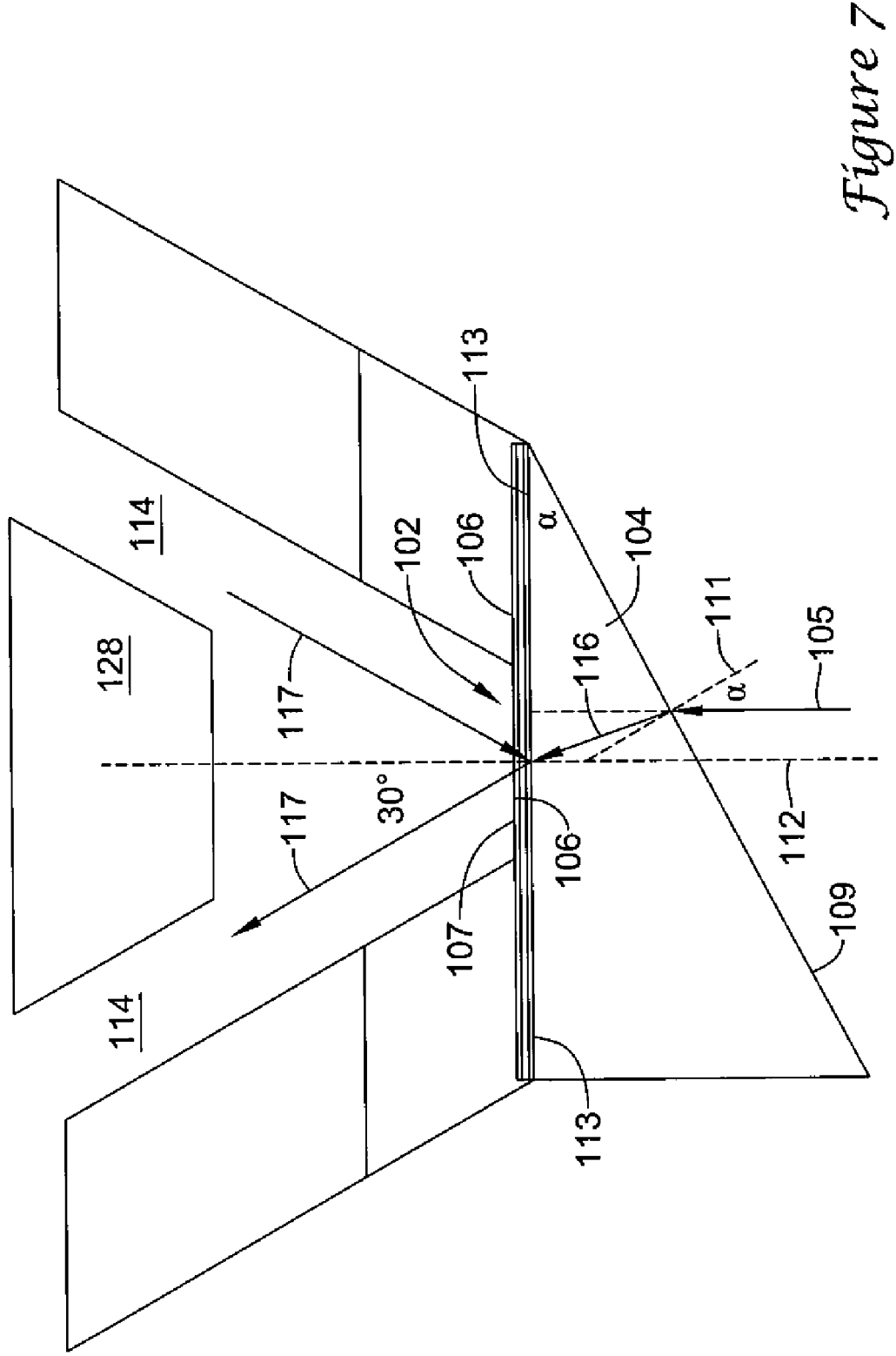
FIG. 7 is a diagram of an input to a cavity of a sensor showing the light path from the source into the cavity via a refracting mechanism.
Figure 8:
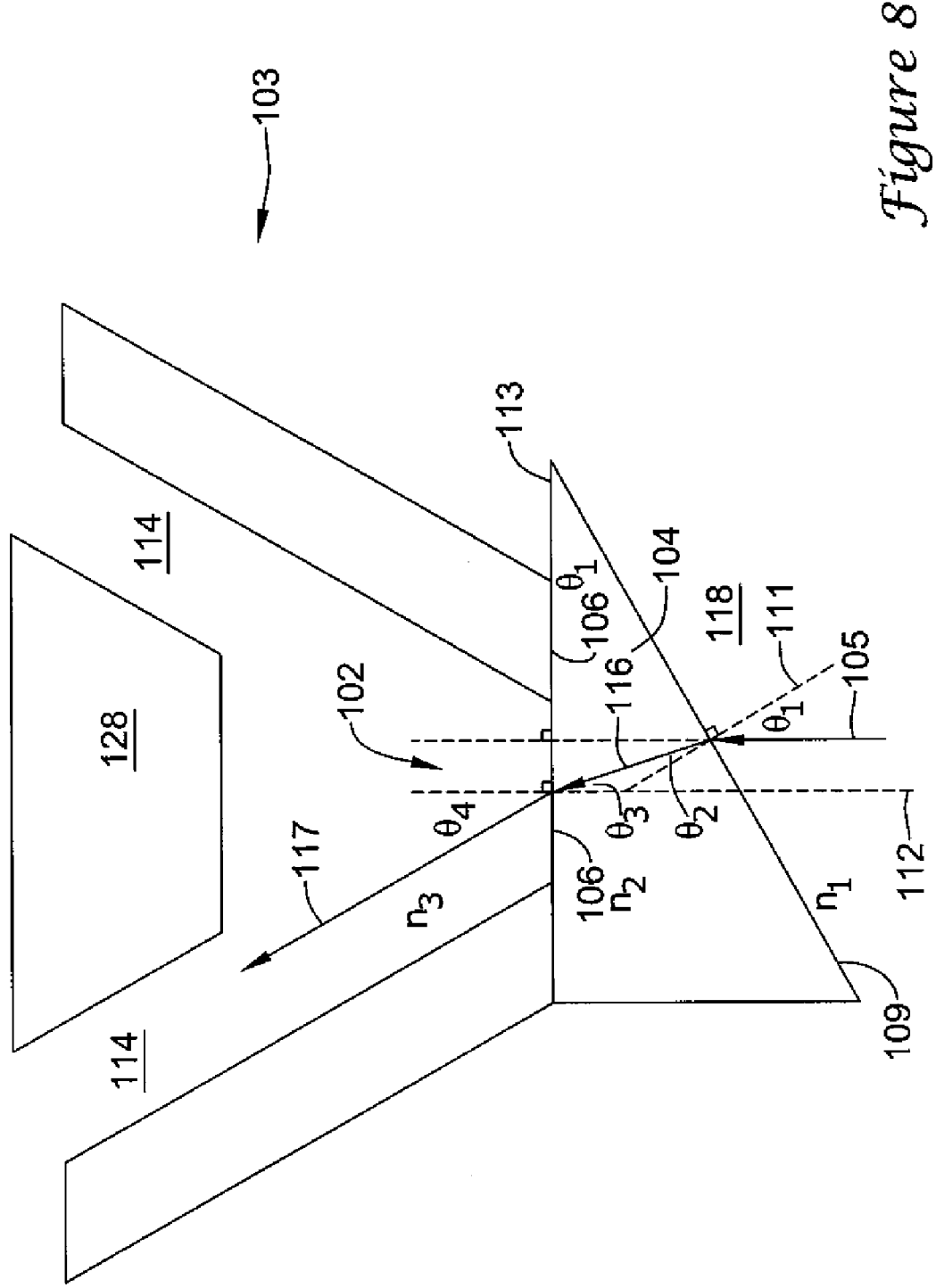
FIG. 8 is a diagram like that of FIG. 7 showing relative angles of the path of light from a source into the cavity of the sensor via the refracting mechanism.

Examples of specific designs are shown in the FIGS. 7-11. FIG. 8 shows angles of light directions relative to the various media, which may facilitate generating an approach to meet a set of specific design requirements (i.e., prism material, cavity angle, prism angle, and so on).

The present approach and system may consist of the external light source 101 (such as a tunable laser), a mechanism for rapidly extinguishing the incident light, an external detector, and the ring-cavity 103 with high reflectance mirrors. The ring cavity should have an optical input port, and optical output port, and gas inlet and outlet ports. The optical input port and the optical output port may be the same physical port in the cavity. Each input, output port in the cavity may be terminated with a high reflectance mirror. There may be is at least one additional high reflectance mirror in the optical path of the ring cavity. The ring cavity may have several mirrors.

The present system may use the input-output prism 104 for both sensing of ring-down cavity light and input light from the laser 101 to a single detector. The present system may specifically require light 101 emitted by the source to be normal relative to the optical input port 102 of the cavity. This feature may be done to facilitate easy and accurate alignment of the laser 101 to the cavity 103, thus reducing overall cost and improving performance. When alignment is attained, a prism coupler 104 may be affixed to the cavity to direct incident light 105 into the cavity.

The cavity block surface 106 may be denoted by dotted line, which has optically finished (polished) plane for each port 102 and 108. Light source 101 may be installed and adjusted to make a beam normally incident on surface 106 of cavity port 102 such that reflected light is directed back into the light source. With the light source 101 and cavity 103 fixed in aligned position, a prism coupler 104 may be installed on the cavity port 103 (making this the optical input port). The inner face of the prism coupler 104 may have a high reflectance optical coating 107 which is next to and parallel with the surface 106. High reflectance mirrors 110 may then be attached to the remaining cavity ports. One or more of the mirrors 110 may have a slight radius of curvature to facilitate optical stability of the cavity 103. One or more of the mirrors 110 may be integrated with a transducer (piezo-driven or otherwise) to tune the cavity into optical resonance.

Figure 6:
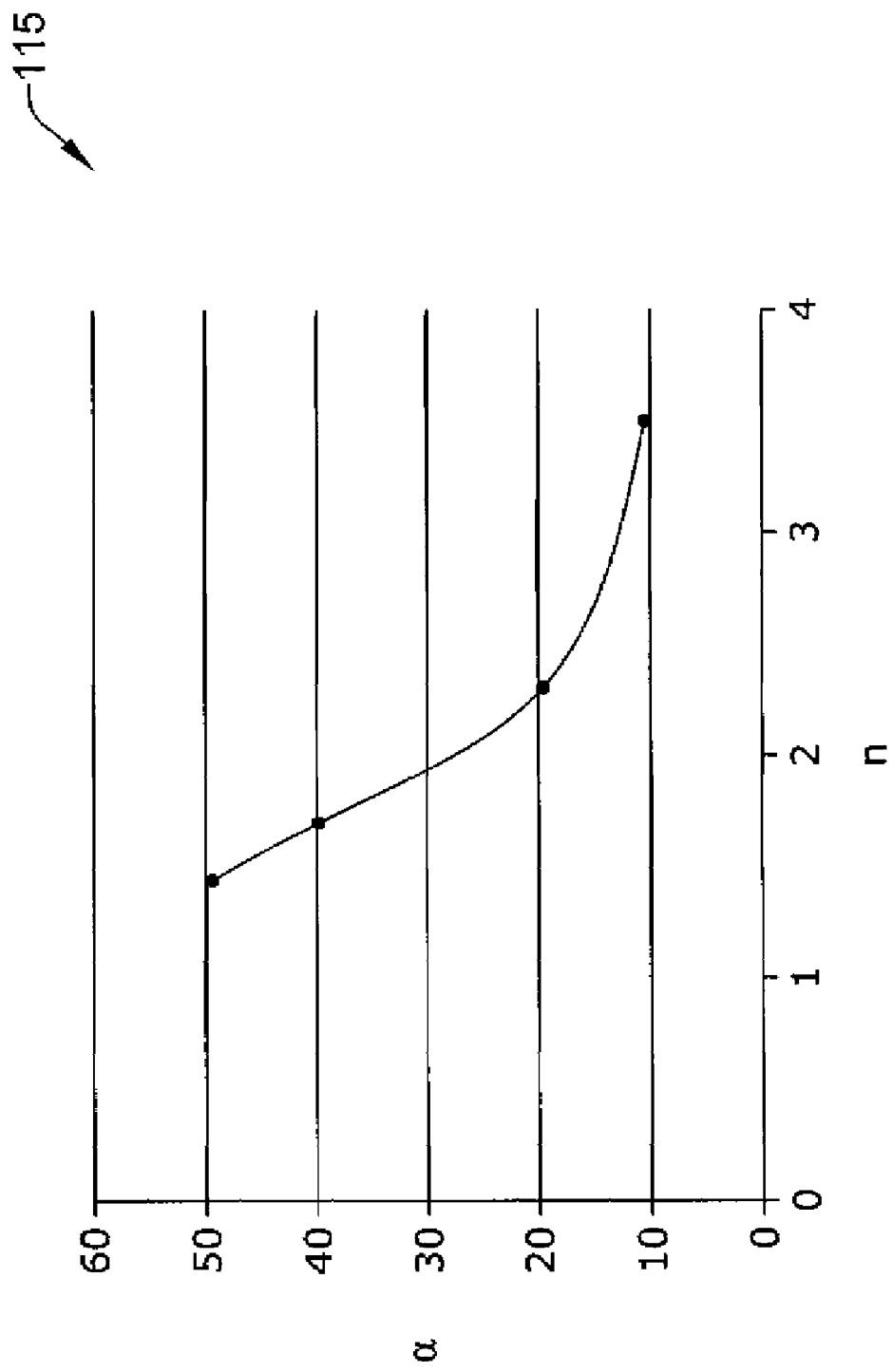
FIG. 6 is a graph of an incident angle of a surface of a refracting mechanism relative to the surface of an input to the sensor cavity versus an index of refraction of the material of the refracting mechanism for a normal input of incident light from the light source for the cavity.

FIG. 6 is a graph 115 showing a relationship of an angle "α" versus the index of refraction "n". The angle is that of the external surface 109 of the prism relative to the surface 106 of the input port 102 or the angle of the incident light 105 relative to a normal 111 of the external surface 109 of the prism 104, as shown in FIG. 7. The incident light 105 may be parallel to a normal 112 of the input port 102 surface 106. Light 105 may be perpendicular to the optical coating 107 and the inside surface or face 113 of the prism 104 facing towards and abutting surface 106 of the input port 102. It would be just a matter of assuring that the beam of light 105 is parallel to the normal 112 of surface 106 of port 102. The is no need of adjusting the beam 105 relative to the normal 112 since it is to be continually maintained as being parallel to the normal 112 or perpendicular to the surfaces 106 and 113, and the optical coating 107. The adjustable factors relative to aligning the light beam so that goes through a path 114 may include the index of refraction n and the angle α of the outside surface 109 relative to the inside surface 113 of the prism 104.

FIG. 8 is a diagram showing the geometrical and physical relationships of the components. One may take $\theta_1 = \alpha$. Incident light 105 may enter the prism at a normal relative to the surface 106 of port 102. There may be a normal 111 relative to surface 109 of prism 104. A path of the incident light 105 may at an angle $\theta_1$ relative to the normal 111. As the incident light 105 enters the prism 104 it may become light 116 which takes a path situated at an angle $\theta_2$ relative to the normal 111. This angle may be calculated using Snell's law in a formula, $n_1 \sin \theta_1 = n_2 \sin \theta_2$, where $n_1$ is the index of refraction of a medium 118, which may be air or some sort of a vacuum, and $n_2$ is the index of refraction of the material of prism 104. The path of light 116 may have an angle $\theta_3$ relative to the normal 112 of the port surface 106. It may be noted that $\theta_1 = \theta_2 + \theta_3$. Light 116 may exit prism 104 at the prism surface 113 and enter the port 102 at the port surface 106 as light 117 into cavity 103 in the path 114 having an angle $\theta_4$ relative to the normal 112. The angle $\theta_4$ may be calculated with a formula, $n_2 \sin \theta_3 = n_3 \sin \theta_4$, where $n_3$ is the index of refraction of the medium in the cavity 103. If the reflective coating on surface 113 situated on the surface 106 of port 102, as shown in FIG. 7, has a different index of refraction different than $n_2$ or $n_3$, it should have virtually no effect on the path of the light 117 in the cavity 114 because of its extreme thinness. The design of the present approach for the entering of the incident light normal to the surface 106 of port 102 may consider the angle that light 117 enters cavity 114 so that it follows a path around in the cavity 114. In an illustrative example of FIG. 7, the angle may be about 30 degrees. With the information of FIGS. 7 and 8, including $n_3$ of the cavity 103 medium that the path 114 is in, and the prism material index of refraction $n_2$, the index of refraction $n_1$ of ambient environment of the light 105, then what the angle $\theta_1$ of surface 109 relative to surface 113 of the prism should be may be tabulated.

Figure 9:
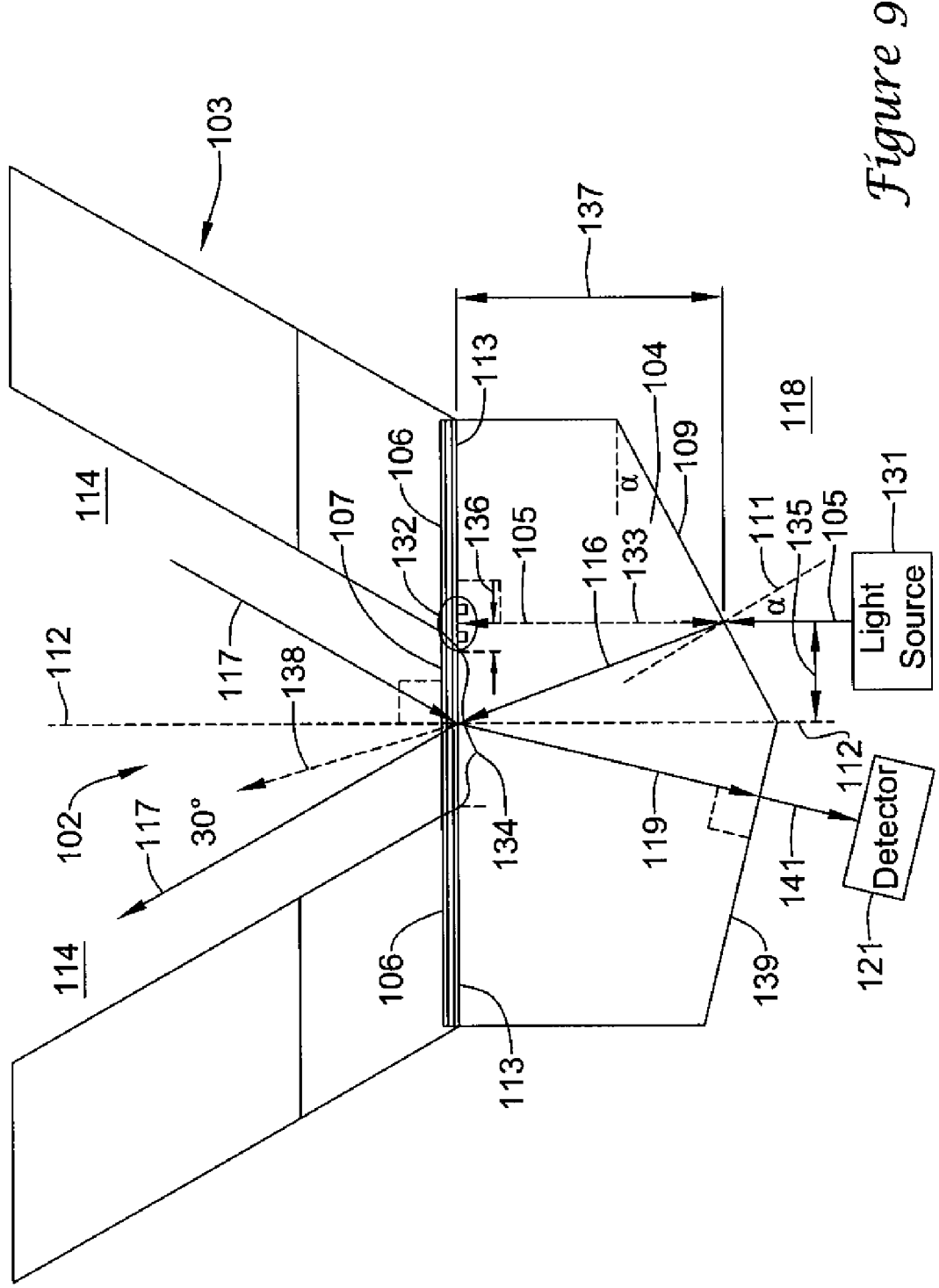
FIG. 9 is a diagram of an input and output incorporating a refracting mechanism and a detector.

Input port 102 may also be an output port for the cavity 114, as shown in FIG. 9. The input and output may be integrated into a common optical coupler or port. The highly reflective coating 107 on surface 113 of the prism may maintain much of the light 117 traveling around through the cavity ring light path 114. However, some of the light 117 may exit from the cavity 103 through the port 102 and prism 104 as light 119. The light 119 may go directly to a detector 121 next to a surface of prism 104 or detector 121 may be a certain distance from the prism as light 119 may exit the prism to propagate the certain distance before being sensed by detector 121. Of the light that may exit the cavity, virtually none of the light from the cavity goes to the light source 131, even though the incident light 105 may have a direction that is normal to the surface of port 102 of the ring cavity 103.

In FIG. 9, if the prism 104 is absent, then light beam 105 from light source 131 may continue on in a direction perpendicular to the surface 106 of port 102. Beam 105 may impinge surface 106 in an area of 132. At a point beyond the prism 104 at surface 109, beam 105 may be regarded as a beam 133 including the reflected beam from the surface at area 132. Beam 133 may be reflected back to light source 131, when the prism 104 is not present. If the light beam 105 and/or 133 is over an area 134 which is an aperture of port 102, then the light 105/133 could still be reflected back toward the light source 131 since surface 106 may extend over the aperture area 134. The distance 135 of the light beam 105 should be sufficient so that the light 105/133 can impinge an area outside of 134. Area 132 may be sufficiently outside of area 134. The impinging of light beam 105/133 on the surface 106 may be about distance 136 away from the aperture area 134.

The light source 131 may be put in place and aligned about the time or after cavity 103 is fabricated but before prism 104 is put in place on the surface 106 of the port 102. The next step of alignment of light source 131 may be to indicate an amount of distance 135 that the beam 105/133 is to be from the normal axis 112. The factors which determine distance 135 may include the index of refraction of the prism 104, the angle α of the surface 109 relative to where the beam 105 enters the prism, the distance 137 that beam 105 is from the surface 106 at the pint of entry into prism 104 at surface 109 in a direction that is parallel to the normal 112, the index of refraction of the matter in the cavity 103, and the angle of a light beam 117 emerging from prism 104 relative to the normal 112 into the cavity via port 102. An increase of distance 137 may increase the distance 135 if beam 105 and its subsequent beam 116 go through the prism 104 to the surface 106 line at about the center of aperture area 132. If the index of refraction were to be the same in the path 114 of cavity 103 as the index of prism 104, then beam 116 would continue in a straight line and take a beam path 138. However, upon the exit of beam 116 from prism 104, having its own index of refraction, to cavity path 114 of cavity 103, beam 116 may become a beam 117 in the cavity 103 having a different index of refraction similar to that of air. There may be a sample gas in path 114 resulting in an index of refraction also similar to that of air. So, various samples in cavity 103 should not significantly vary the index of refraction in the cavity.

To align the light source 131 relative to the cavity 103, a predetermined spot, mark or some other indicator may be provided on surface 106 of port 102 of cavity 103. With the light beam 105/133 parallel to the normal 112, light source 131 may be moved in an x and/or y direction, which is movement parallel to surface 106, to get the beam 105/133 to impinge a spot within area 132. Upon impingement of that spot, a beam 133 may be retro-reflected back to light source 131 which affects the light source or some kind of detector which may situated at the location of the light source or inside the light source 131. The return of light 133 to light source along the path of beam 105 may also noticeably affect performance of the light source thereby indicating a correct alignment. The spot within area 132 on surface 106 may be a mirror or some other reflective mechanism. The area may have notches within the area where the light beam 105 may be focused before fixing the light source 131 in its position. The alignment spot in area 132 may instead be a detector of some kind. There may be other ways of aligning the light source 131 and/or its beam 105. The light source 131 may have a fixture already prepared which may result in automatic alignment upon installation of source 131.

A pre-determined alignment of the light source 131 may be achieved to provide cost-effective producibility of the present optical cavity system. Also, using ring-laser gyroscope components or fabrication for the cavity 103 may also improve the cost-effectiveness of making the present system.

When prism 104 is place into position, and beams 105, 116 and 117 proceed about their paths, a return beam 117 from the cavity 103 back into prism 104, due to the semi-transmissive property of the reflective optical coating, film or mirror 107, may result partially as a beam 119 going through prism 104 away from cavity 103 and exiting the prism 104 through a surface 139. Beam 119 may emerge as a beam 141. Beam 141 may be detected by a detector 121. Detector 121 output may be connected to a processor (not shown) or the like for analysis, calculation, interpretation and so forth of the output.

Prism 104 may have the face or surface 139 of prism 104 fabricated, shaped or cut at an angle so that beam 119 impinges surface 139 at a normal. Thus, beam 141 may emerge from prism 104 parallel to a normal of the surface 139.

Figure 10:
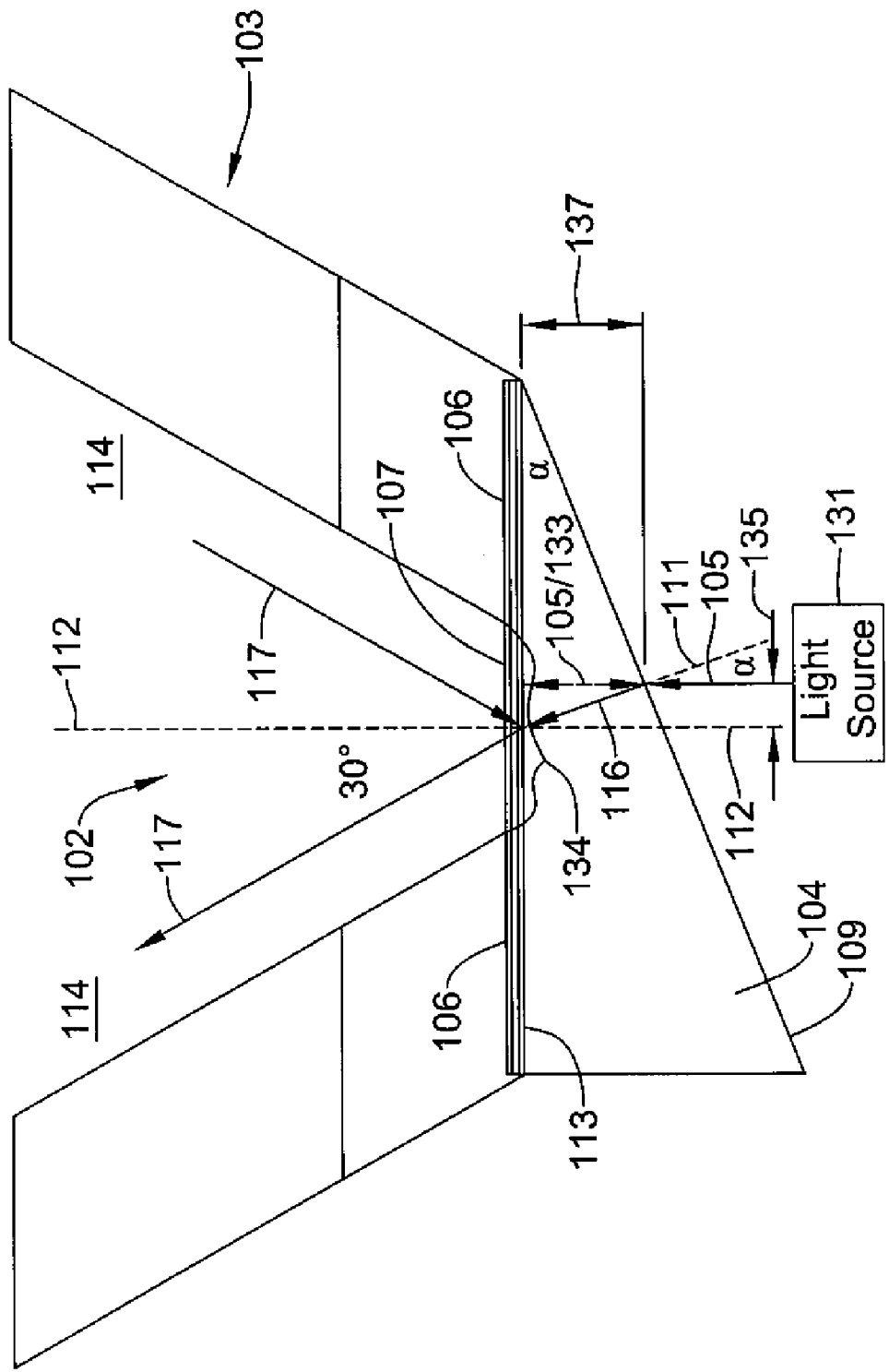
FIGS. 10 and 11 show inputs having prisms of significantly differing indices of refraction but with the same incident light and cavity light path angles.

In FIG. 10, in comparison to FIG. 9, it may be noted that if the distance 137 is shorter because of a thinner prism 104, then the distance 135 is shorter. In FIG. 10, the alignment might not be similarly effected as in the setup in FIG. 9, because without the prism 104 in a setup alignment of source 131, light beam 105/133 would be in the aperture area 134 of port 102 and may depend on surface 106 to have a reflector, mark, detector or the like for acknowledgement of the beam 105/133 relative to an alignment of source 131 before an installation of the prism 104. However, a thicker prism 104 having a greater distance 137 may result in a greater distance 135 so that an alignment beam 105/133 may impinge a part of the cavity 103 block in an area outside of the aperture area 134.

Figure 11:
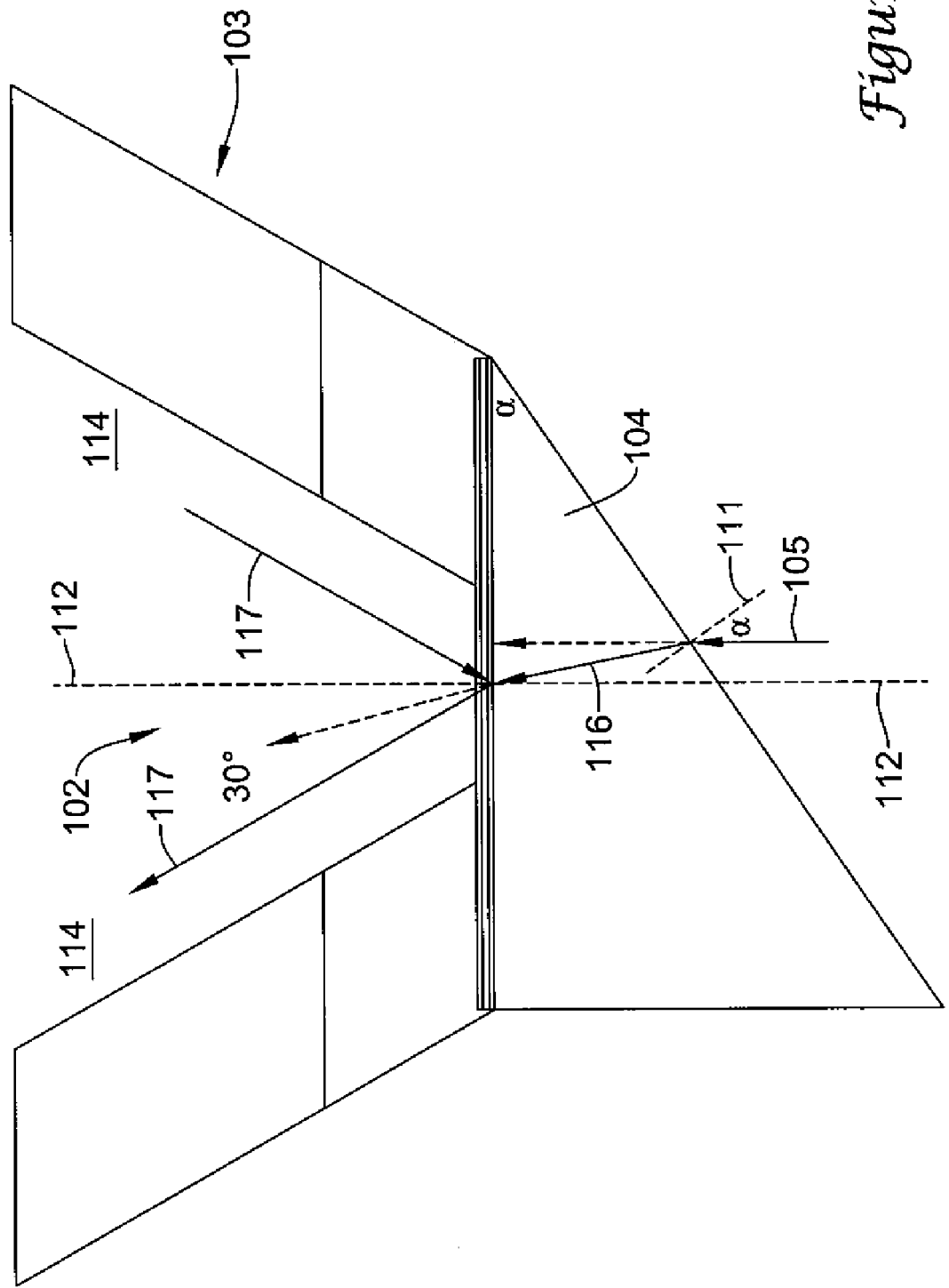

The diagrams of FIG. 10 and FIG. 11 appear similar to each other that the angle α of the prism 104 in FIG. 10 appears smaller than angle α of the prism 104 in FIG. 11. The prism of FIG. 10 may be silicon whereas the prism of FIG. 11 may be glass, having indices of refraction at about 4.0 and 1.5, respectively. The angles α may be about 11.3 and 50.5 degrees, respectively. Graph 115 of FIG. 6 illustrates the relationship between the angle α and the index of refraction n of the prism.

Figure 12:
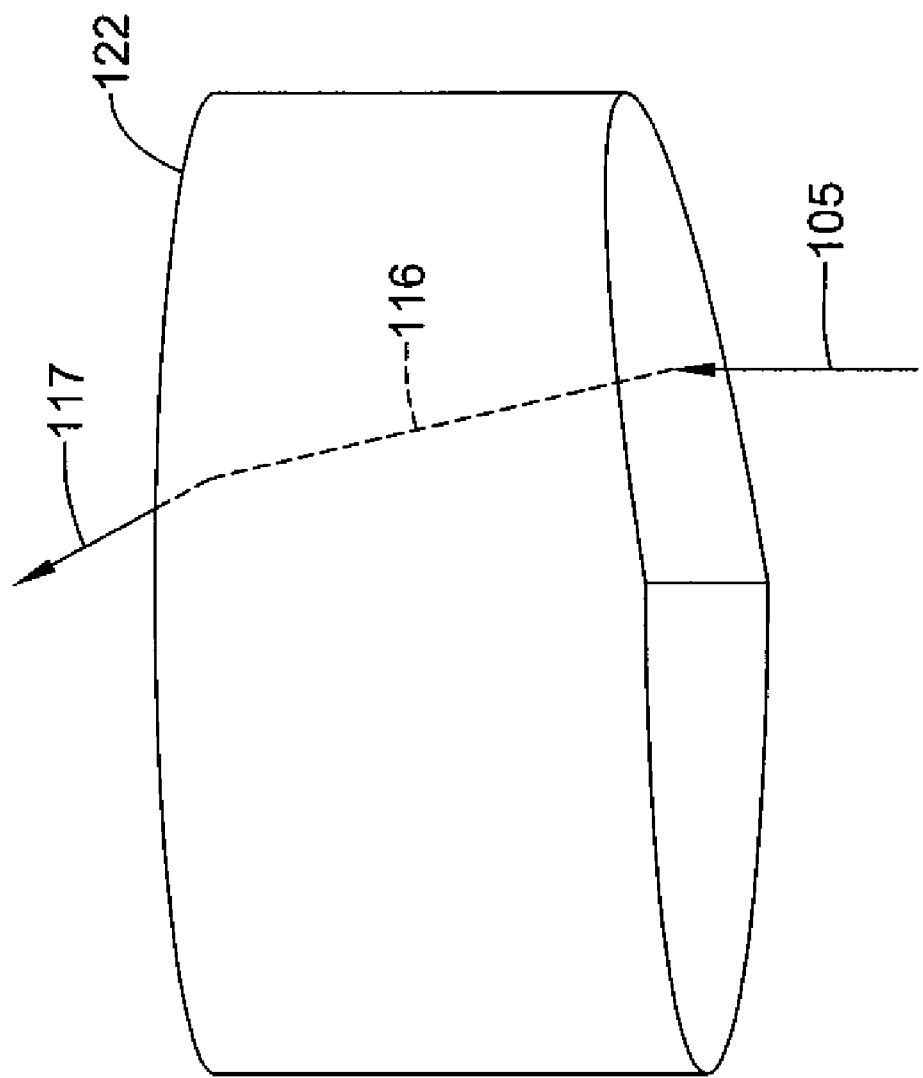
FIGS. 12 and 13 are diagrams of example refracting mechanisms that may be formed on an input of a machined block cavity like that shown in FIG. 3.
Figure 13:
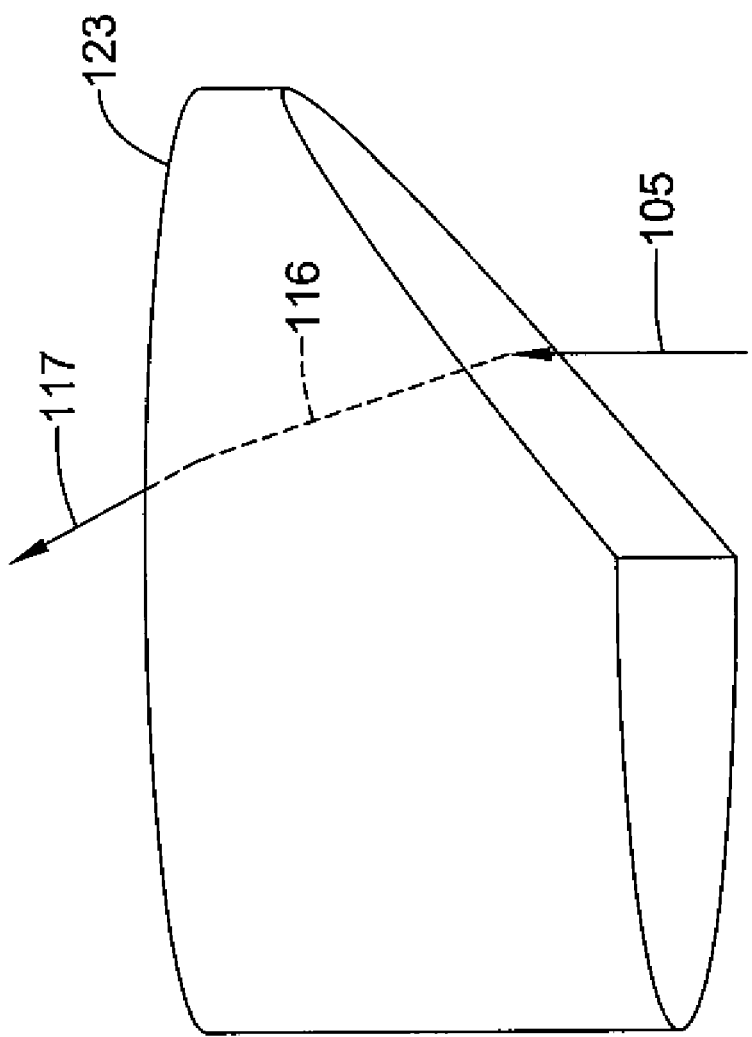

FIGS. 12 and 13 are diagrams of example refracting mechanisms 122 and 123 that may be an implementation of the prisms 104 of FIGS. 10 and 11, respectively. Mechanism 122 or 123 may be adhered to an input of a cavity such as the machined block cavity 312 shown in FIG. 3. A production technique of various kinds may be used to make mechanism 122 or 123a part of cavity 312.

Figure 14:
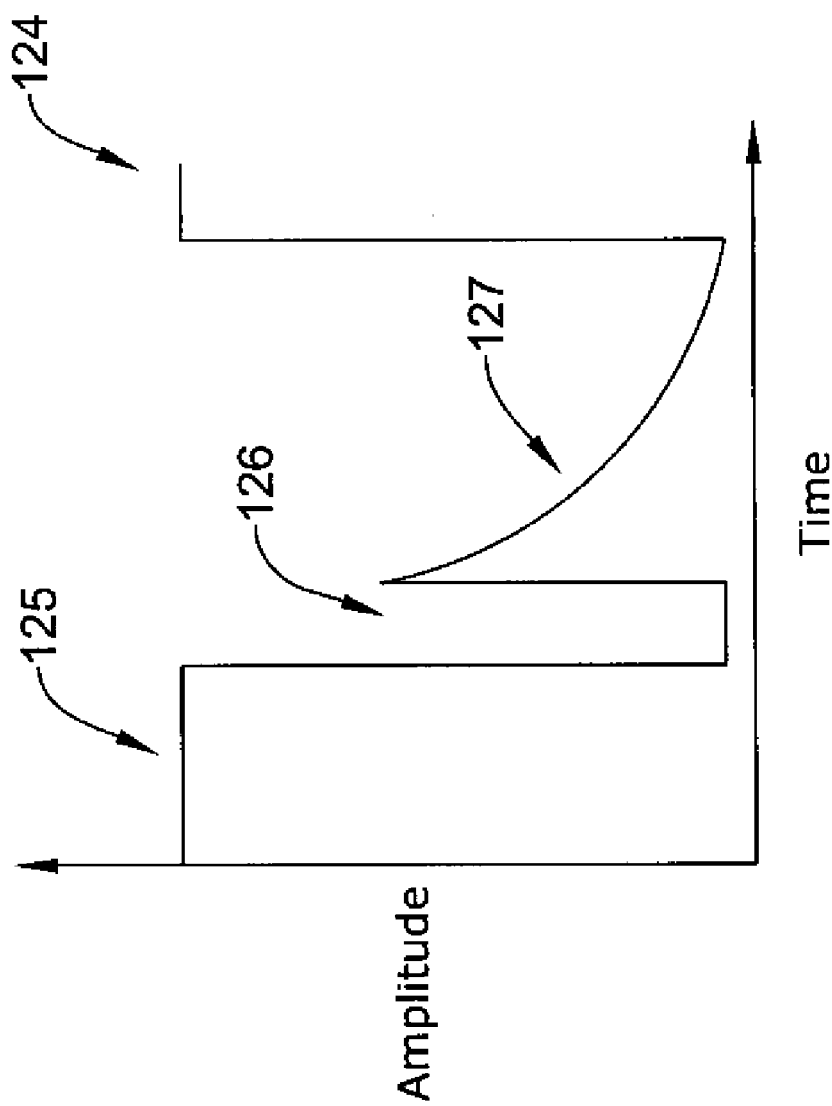
FIG. 14 is a graph of an application of the cavity of the device being utilized as a cavity ring down sensor.

FIG. 14 is a graph 124 of an application of the cavity of the device shown in some of the Figures discussed herein being utilized as a cavity ring down sensor. The graph shows amplitude versus time. Detector 121 of the setup shown in FIG. 9 may be a multi function detector which senses intensity of light to the cavity 103 in one function, as shown by a portion 125 of graph 124. Another function of the of the detector 121 may include coupling to the cavity at portion 126 and measuring the light signal in the cavity after at portion 127 after a supply of light to the cavity ceases at the coupling portion 126. Portion 127 shows a decay of the cavity light amplitude of a cavity ring down device. The amplitude and the time of the ring down may provide information about a sample fluid which may in the cavity 103. Also, wavelength of the light and absorption properties of the sample may be useful. A processor (e.g., processor 63 or 722 of FIGS. 1 and 2, respectively) along with other items such as tables and algorithms may aid in determining information about the sample.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A method for sensing comprising:
    providing light from a source to an input of a chamber having a closed light path formed by three or more mirrors, in a direction parallel to a normal of the input; and
    detecting light from the light path through an output of the chamber; and
    wherein:
    the light is provided into the light path of the chamber via a refracting optics and the input;
    the input is for conveying the light into the light path through a mirror of the three or more mirrors;
    the mirror of the three or more mirrors comprises a planar surface; and
    the normal of the input is perpendicular to the planar surface.

2. The method of claim 1, wherein:
    a position of the light relative to the input is determined according to an alignment indicator proximate to the input; and
    the alignment indicator is located relative to the input according to at least one or more parameters of the refracting optics.

3. The method of claim 2, further comprising:
    injecting a fluid sample into the chamber; and
    measuring at least one parameter of the light from the output of the chamber which is indicative of a property of the fluid sample.

4. The method of claim 3, further comprising processing the at least one parameter of the light from the chamber to determine an identity of the sample and/or a concentration of the sample in the chamber.

5. The method of claim 3, wherein the at least one parameter of the light is a period of time that light remains in the path after a ceasing of the providing light to the input of the chamber.

6. The method of claim 1, wherein:
the refracting optics is a prism having a first surface for entry of light and a second surface for exit of the light to the input of the chamber; and
a first angle between the first surface and second surface has a magnitude set for the light to enter the light path from the second surface in alignment with the light path upon entry from the input of the chamber.

7. The method of claim 6, wherein:
the second surface is perpendicular to the normal of the input;
the light goes through the prism at a second angle relative to a normal of the first surface;
the light exits the second surface at a third angle relative to the normal of the input;
$n_1 \sin\theta_1 = n_2 \sin\theta_2$;
$n_2 \sin(\theta_1 - \theta_2) = n_3 \sin\theta_3$;
$n_1$ is an index of refraction of a medium of the incident light beam to the first surface;
$n_2$ is an index of refraction of the medium in the prism;
$n_3$ is an index of refraction of the medium in the light path;
$\theta_1$ is the first angle;
$\theta_2$ is the second angle; and
$\theta_3$ is the third angle.

8. A sensor system comprising:
a cavity having a ring-like light path of three or more mirrors for propagation of light;
an optical input connected to a first mirror of the three or more mirrors for entering light into the ring-like path of the cavity;
a light refracting prism optically connected to the input; and
a source for providing light to the prism, the light having a direction approximately parallel to a normal of the input; and
wherein:
the first mirror has a planar reflecting surface; and
the normal of the input is perpendicular to the planar reflecting surface.

9. The system of claim 8, further comprising:
an alignment indicator proximate to the input; and
wherein:
a location of the alignment indicator is determined according to relevant optical properties of the light refracting prism; and
the source is aligned according to the indicator so that the light from the source has a direction approximately parallel to the normal of the input.

10. The system of claim 8, further comprising:
a port connected to the cavity for conveying a sample of fluid into the cavity;
an optical output connected to the cavity; and
a detector proximate to the optical output for measuring one or more parameters of light from the cavity via the output.

11. The system of claim 10, further comprising:
readout electronics connected to the detector; and
wherein the readout electronics comprises a dual FET charge amplifier.

12. The system of claim 8, wherein the cavity is situated in a ring laser gyroscope structure.

13. The system of claim 8, wherein the light path is tunable to a particular wavelength.

14. An optical system comprising:
a cavity having three or more corners for providing a closed loop light path in the cavity, each corner having a reflecting surface; and
a refracting mechanism; and
wherein:
at least one reflecting surface comprises an optical lane and an input port;
the refracting mechanism has a first surface proximate to the optical plane and input port of the at least one reflecting surface;
the refracting mechanism has a second surface for receiving a light beam parallel to a normal to the optical plane of the at least one reflecting surface; and
the refracting mechanism is for refracting the light beam through the optical plane and input port to be in a direction parallel to a proximate portion of the light path in the cavity.

15. The system of claim 14, further comprising:
a light source for providing the light beam; and
wherein:
the light source is aligned relative to an alignment indicator situated on the cavity; and
the alignment indicator is for adjusting a light beam from the light source parallel to the normal to the optical plane of the at least one reflecting surface.

16. The system of claim 15, wherein:
a location of the alignment indicator determined according to one or more parameters of the refracting mechanism; and
the light source is aligned prior to a placement of the refracting mechanism.

17. The system of claim 14, further comprising:
a light source for providing the light beam;
an output coupled to the light path;
a light detector optically connected to the output;
a port connected to the cavity for entering a fluid sample in the cavity; and
a processor connected to the light detector for measuring a decay of intensity of light in the light path after the light source stops providing the light beam.

18. The system of claim 14, wherein:
the cavity is situated in a block of material and comprising a plurality of bores in the block connected end to end; and
the light path from bore to another bore is connected with a reflecting surface situated between the bores.

19. The system of claim 18, wherein at least one reflecting surface is moveable for adjusting a length of the light path to tune the path for a particular wavelength.

20. The system of claim 17, wherein the light source is tunable for providing the light beam having a wavelength for absorption by at least a portion of the fluid sample.

* * * * *